(12) United States Patent
Watanabe

(10) Patent No.: US 6,325,537 B1
(45) Date of Patent: Dec. 4, 2001

(54) X-RAY DIAGNOSIS APPARATUS

(75) Inventor: Naoto Watanabe, Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/393,195

(22) Filed: Sep. 10, 1999

(30) Foreign Application Priority Data

Oct. 16, 1998 (JP) .................................................. 10-295526

(51) Int. Cl.[7] .................................. H05G 1/02; A61B 6/00
(52) U.S. Cl. ............................................... 378/197; 378/196
(58) Field of Search .................................... 378/197, 193, 378/196, 195, 198, 4, 20, 181

(56) References Cited

U.S. PATENT DOCUMENTS

| | | | |
|---|---|---|---|
| 5,050,204 | * 9/1991 | Siczek et al. .......................... 378/197 |
| 5,052,036 | * 9/1991 | Grady .................................... 378/197 |
| 5,835,558 | * 11/1998 | Maschke ................................ 378/198 |
| 6,092,928 | * 7/2000 | Mattson et al. ....................... 378/98.2 |

\* cited by examiner

Primary Examiner—Drew Dunn
(74) Attorney, Agent, or Firm—Oblon, Spivak, McClelland, Maier & Neustadt, P.C.

(57) ABSTRACT

An X-ray generator is rotatably attached to one end of a C-shaped arm, and a planar X-ray detector is attached to the other end of the C-shaped arm via a link mechanism capable of freely changing a position/direction of the detector. The X-ray generator is rotated to achieve imaging in an oblique direction, without sliding/rotating the C-shaped arm. The link mechanism is driven in association with the rotation of the X-ray generator so that the X-ray detector may face the X-ray generator. Thus, the limit to the slide angle range can substantially be eliminated without degrading accessibility, and various positioning is achieved exactly and easily.

28 Claims, 8 Drawing Sheets

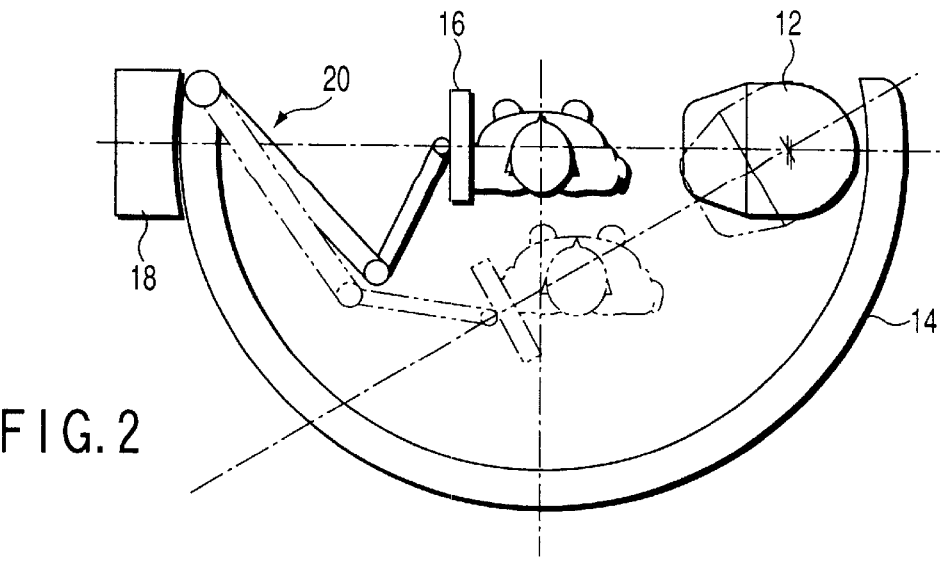
FIG. 2
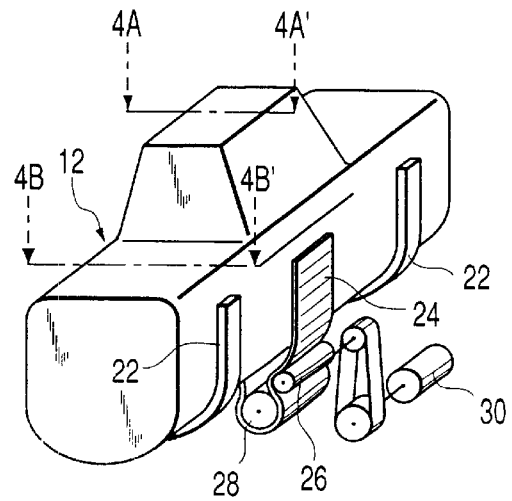
FIG. 3
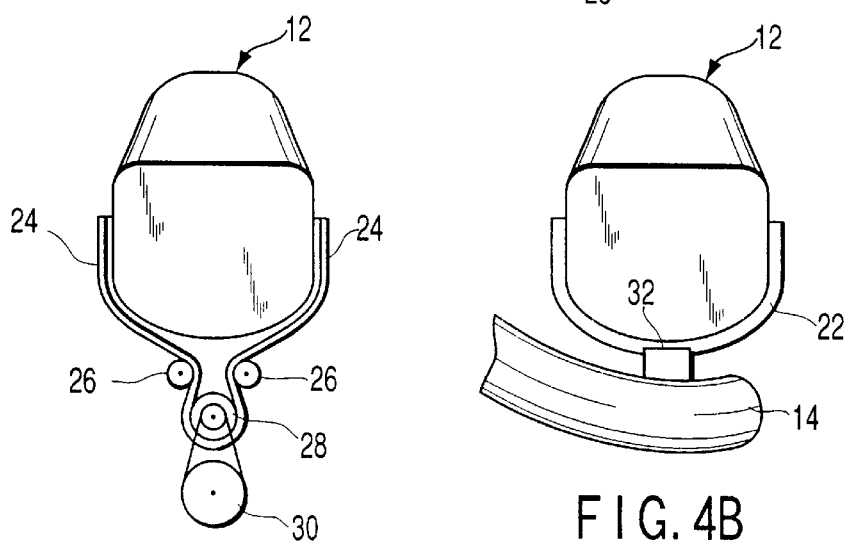
FIG. 4A
FIG. 4B

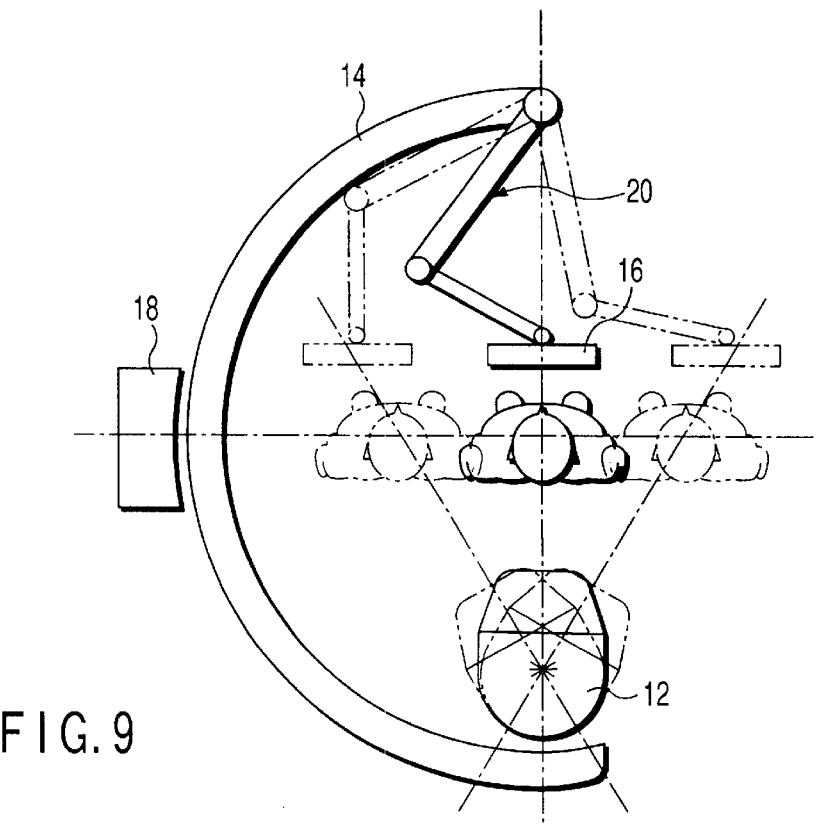
F I G. 9
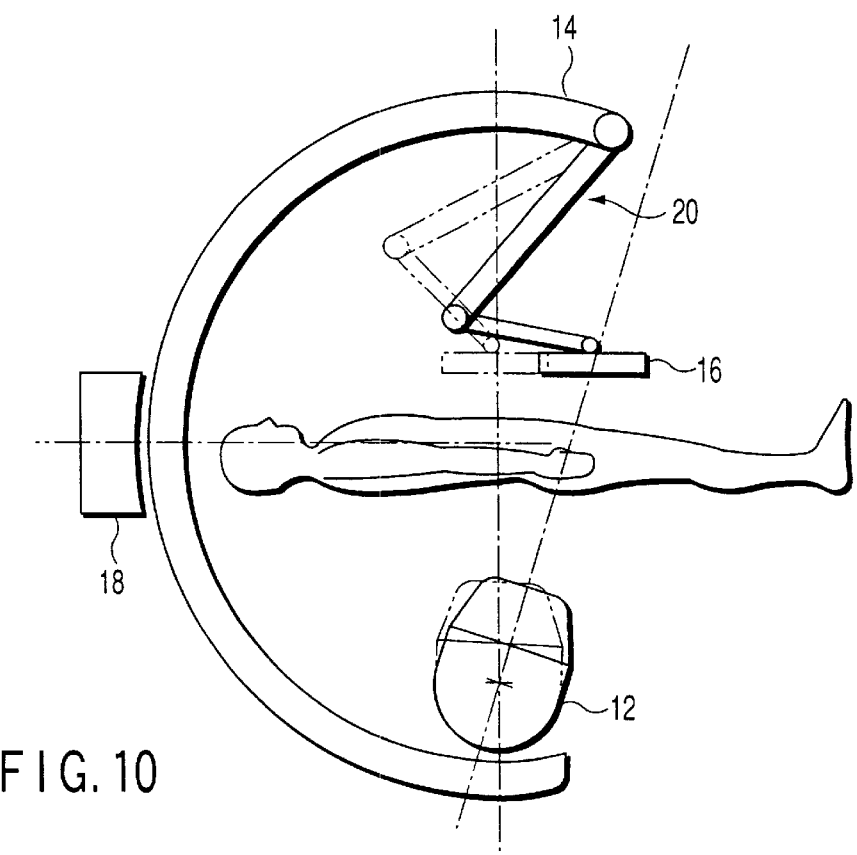
F I G. 10

X-RAY DIAGNOSIS APPARATUS

BACKGROUND OF THE INVENTION

The present invention generally relates to an X-ray diagnosis apparatus, and more particularly to an improvement of an arm for holding an X-ray generator and an X-ray detector.

This application is based on Japanese Patent Application No. 10-295526, filed Oct. 16, 1998, the entire content of which is incorporated herein by reference.

An example of the X-ray diagnosis apparatus is an X-ray diagnosis apparatus for a circulatory system. In this example, an X-ray generator and an X-ray detector are fixed to both ends of the arm so as to face each other. In general, there are two shapes of the arm, i.e. C-shape and U-shape. The C-shaped arm is now widely used in view of the efficiency of 3D positioning.

FIG. 1 shows a conventional circulatory-system X-ray diagnosis apparatus using the C-shaped arm. The C-shaped arm 103 is slidably held by a holder 102. The holder 102 is held to a support column 101 so as to be rotatable about a major axis (axis A1 in FIG. 1). The support column 101 is attached to a ceiling 100 or the floor so as to be rotatable about a support column axis (axis A2 in FIG. 1). Although not shown, a vertical drive mechanism may be provided on the ceiling 101. In the case of a ceiling-pending type apparatus, a rail is provided on the ceiling so that the apparatus may be movable in one or two directions.

The X-ray detector 105 includes an image intensifier (I.I.). The X-ray detector 105 converts X-ray information, which has passed through an object, to optical information and converges the optical information through an optical lens. The converged information is taken into a TV camera for image display. The X-ray detector 105 can be vertically moved by a drive mechanism (in directions toward and away from the X-ray generator 104).

The X-ray detector 105 (including the I.I., optical system, TV camera, etc.) and X-ray generator 104 are fixed to both ends of the C-shaped arm 103 so as to face each other. A rail (not shown) is provided on a rear surface or a side surface of the C-shaped arm 103. Rolls (not shown) provided on the holder 102 clamp the rail, whereby the C-shaped arm 103 is slidably held.

Because of the structure of the C-shaped arm 103, the range of angles over which the C-shaped arm 103 can slide is limited (180°). On the other hand, with development and diversification of operation techniques, there is a demand for observation of finer vascular images with no overlapping with non-related blood vessels. Specifically, there is a demand for an increase in the slide angle of the C-shaped arm, which will permit image acquisition at greater angles.

To meet the demand, there is an idea that the C-shaped arm 103 is extended to increase the slide stroke. If the C-shaped arm 103 is extended, however, the end portions of the C-shaped arm 103 may physically interfere with the object, depending on the direction of access to the object, in particular, when the head portion of the object is accessed by the C-shaped arm 103. Consequently, the slide stroke may decrease, contrary to the expected result.

On the other hand, there is an idea that images are acquired while the C-shaped arm is rotated about the major axis and the projection images are three-dimensionally reconstructed to obtain a 3D image. This idea is based on the fact that the slide stroke of the C-shaped arm is limited, as stated above, and there is difficulty in acquiring all image information necessary for 3D reconstruction. When the image acquisition is effected based on the major axis rotation, there is no choice but to access the head portion of the object in order to avoid interference between the C-shaped arm and the head of the object. Therefore, the region of application of the apparatus is restricted.

Furthermore, there is an idea that the C-shaped arm is rotated around the object to obtain tomographic images. In this case, however, the angle of X-ray detection plane to the object varies and non-linear conversion needs to be performed according to the rotation angle after image acquisition. There arise such problems as degradation in image quality and an increase in time needed up to image display.

In the meantime, there is known a circulatory-system X-ray diagnosis apparatus wherein the arm is formed in a ring shape, like the X-ray computer tomography apparatus, so as to obtain a 3D-reconstructed image, the X-ray generator and X-ray detector are disposed on the arm so as to face each other, and the ring-shaped arm is made rotatable so as to perform volume scan. This apparatus can rotate in a sliding manner over 360°0 and can acquire a 3D image by 3D reconstruction. However, the ring-shaped arm has no such opening as in the C-shaped arm, and the access to the object is very difficult.

The above drawbacks are present not only in the circulatory-system X-ray diagnosis apparatus but in other X-ray diagnosis apparatuses.

BRIEF SUMMARY OF THE INVENTION

The present invention has been made in consideration of the above circumstances, and its object is to provide an X-ray diagnosis apparatus capable of exactly and easily achieving various positioning and applicable to a wide range of diagnostic uses.

According to the present invention, there is provided following apparatuses.

(1) An X-ray diagnosis apparatus comprises:
- an X-ray generator for emitting X-rays towards an object;
- an X-ray detector for detecting the X-rays which have passed through the object;
- a first arm;
- an arm support member for supporting the first arm;
- a detector support member, provided at one end of the first arm, for supporting the X-ray detector such that a position/direction of the X-ray detector is variable; and
- an X-ray generator support member, provided at the other end of the first arm, for supporting the X-ray generator such that a position/direction of the X-ray generator is variable.

(2) In the apparatus (1), the arm support member comprises a holder for slidably supporting the first arm, and a support column for rotatably supporting the holder.

(3) In the apparatus (2), the first arm has an arcuated shape.

(4) In the apparatus (1), the detector support member comprises a plurality of arms and a joint for movably coupling the arms, one of the arms being movably coupled to the one end of the first arm, and another of the arms being movably coupled to the detector.

(5) In the apparatus (1), the X-ray generator support member comprises a plurality of arms and a joint for movably coupling the arms, one of the arms being movably coupled to the other end of the first arm, and another of the arms being movably coupled to the X-ray generator.

(6) In the apparatus (1), the detector support member comprises a single extendible arm movably coupled at one end to the one end of the first arm and movably coupled at the other end to the detector.

(7) In the apparatus (1), the X-ray generator support member comprises a single extendible arm movably coupled at one end to the other end of the first arm and movably coupled at the other end to the X-ray generator.

(8) In the apparatus (1), the detector support member controls the position/direction of the detector such that a center of the emitted X-rays coincides with a center of an image reception plane of the detector, and the X-ray generator controls an X-ray aperture opening in accordance with a positional relationship between the X-ray generator and the X-ray detector.

(9) In the apparatus (1), the detector support member controls the position/direction of the X-ray detector such that the X-ray detector faces the X-ray generator.

(10) In the apparatus (9), the detector support member supports the X-ray detector such that a distance (SID) between a focus point of the X-ray generator and a detection plane of the X-ray generator is kept constant.

(11) In the apparatus (1), the detector support member controls the position/direction of the X-ray detector such that the X-ray detector is parallel to a floor.

(12) The apparatus (11) further comprises:

a bed apparatus for parallel-moving the object in a plane parallel to the floor, and wherein the X-ray generator support member changes the position/direction of the X-ray generator in association with movement of the object, and the detector support member parallel-moves the X-ray detector in a plane parallel to the floor in association with the movement of the object.

(13) In the apparatus (11), the X-ray generator support member changes the position/direction of the X-ray generator such that a direction of the X-rays varies along a body axis of the object, and the detector support member parallel-moves the X-ray detector in a plane parallel to the floor in association with a change in the position/direction of the X-ray generator.

(14) In the apparatus (1), the detector support member controls the direction of the X-ray detector at a predetermined angle to the floor.

(15) In the apparatus (1), the detector support member controls the position/direction of the X-ray detector such that the X-ray detector is substantially put in close contact with a body surface of the object.

(16) The apparatus (1) further comprises a handle provided on a part of one of the detector support member and the detector, and wherein the X-ray generator support member moves the x-ray generator in association with movement of the X-ray detector when the X-ray detector is manually moved with use of the handle.

(17) In the apparatus (1), the detector support member comprises input means for setting a distance between a focal point of the X-ray generator and a detection plane of the X-ray detector, means for controlling the position/direction of the X-ray detector such that the distance is kept constant, and display means for displaying the set distance.

(18) The apparatus (1) further comprises means for controlling a position of a bed, on which the object is placed, such that a center of an X-ray flux passes through a center of a region-of-interest of the object while an imaging magnification ratio is kept constant.

(19) In the apparatus (1), the detector support member includes means for moving the X-ray detector in a given plane, and the X-ray generator support member includes means for controlling an X-ray aperture opening of the X-ray generator such that a center of an X-ray flux coincides with a center of a detector image-reception plane of the X-ray detector.

(20) The apparatus (19) further comprises means for controlling a position of a bed, on which the object is placed, such that a region-of-interest is always located at a center of an image.

(21) In the apparatus (1), the detector support member comprises a brake release switch for manually turning on/off braking of respective movable mechanisms.

(22) The apparatus (21) further comprises means for controlling respective movable portions holding the detector support member such that manual operations can be performed when the position/direction of the X-ray detector is controlled.

(23) In the apparatus (20), the X-ray generator support member includes means for controlling an X-ray aperture opening of the X-ray generator such that a center of an X-ray flux coincides with a center of an image-reception plane of the X-ray detector.

(24) In the apparatus (1), the first arm has an arcuated shape of about 90°.

(25) In the apparatus (1), the X-ray detector is a planar detector comprising a plurality of solid-state detection elements.

(26) In the apparatus (2), the first arm is such an offsetless arm that a rotational axis of the holder is located in a plane defined by the arm.

According to the present invention, the X-ray generator for emitting X-rays to the object is attached to the arm such that the position/direction of the X-ray generator is variable. The position/direction of emitted X-rays can be altered by changing the direction of the X-ray generator. The X-ray detector for detecting X-rays, which have passed through the object, is attached to the arm via the mechanism capable of easily changing the position/direction of the X-ray detector in accordance with the direction of emission of X-rays determined by the rotation of the X-ray generator. The bed on which the object is placed is moved to the position corresponding to the direction of emission of X-rays determined by the position/direction of the X-ray generator. Unlike the conventional C-shaped arm, the C-shaped arm of this invention can be positioned at large angles. The degree of freedom of the apparatus increases and this apparatus is applicable to a wide range of clinical uses. Moreover, the slide stroke can be substantially increased without deteriorating the accessibility to the object, and volume image acquisition is realized. Tomographic images can also be obtained with ease, and the degree of freedom of the apparatus increases. Furthermore, the apparatus can be reduced in size and weight.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the present invention and, together with the general description given above and the detailed description of the preferred embodiments given below, serve to explain the principles of the present invention wherein:

FIG. 2 shows a basic structure of a C-shaped arm of an X-ray diagnosis apparatus according to a first embodiment of the present invention;

FIG. 3 is a perspective view showing a rotary mechanism of an X-ray generator according to the first embodiment;

FIGS. 4A and 4B are cross-sectional views of the rotary mechanism of the X-ray generator;

FIG. 9 shows a basic structure of a C-shaped arm of an X-ray diagnosis apparatus according to a second embodiment of the present invention;

FIG. 10 shows another example of the position in the second embodiment;

DETAILED DESCRIPTION OF THE INVENTION

A preferred embodiment of an X-ray diagnosis apparatus according to the present invention will now be described with reference to the accompanying drawings.

First Embodiment

Figure 1:
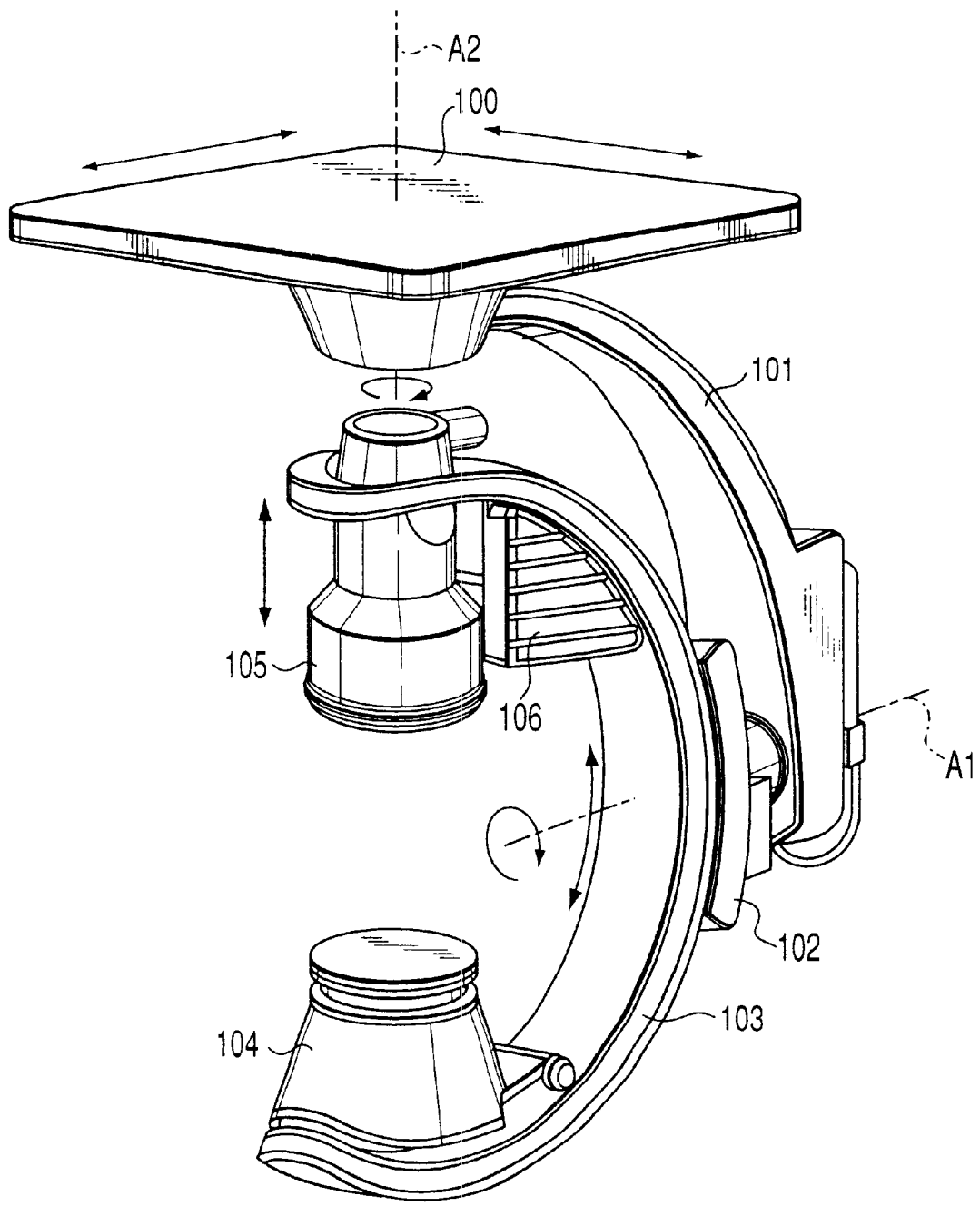
FIG. 1 is a perspective view of a C-shaped arm and associated parts of a conventional circulatory-system X-ray diagnosis apparatus.

FIG. 2 shows a C-shaped arm of an X-ray diagnosis apparatus according to the first embodiment of the present invention. The general structure of the first embodiment is the same as that of the prior art shown in FIG. 1, and the showing of the support column, etc. is omitted. Unlike the prior art, in the first embodiment, an X-ray generator 12 including an X-ray tube is held to one end of a C-shaped arm 14 (having a substantially semicircular shape) such that the position/direction of the X-ray generator 12 can be varied. In addition, a planar X-ray detector 16 in which a plurality of solid-state detector elements are arranged in an array is held to the other end of the C-shaped arm 14 such that the position/direction of the planar X-ray detector 16 can be varied. Various types of holding structures can be adopted. In this embodiment, the position/direction of the planar X-ray detector 16 can be varied but the position of the X-ray generator 12 can not be varied. The X-ray generator 12 is directly held to the C-shaped arm 14 via a rotary mechanism, and the X-ray detector 16 is held to the C-shaped arm 14 via a link mechanism 20 having two arms. However, the X-ray generator 12 can be held to the C-shaped arm 14 via the link mechanism 20 having two arms such that the position/direction of the X-ray generator 12 can be varied.

The direction of the X-ray generator 12 is varied in association with the position/direction of the X-ray detector 16. The rotary mechanism for holding the X-ray generator 12 and the link mechanism 20 for holding the X-ray detector 16 are controlled such that the X-ray detector 16 may always be opposed to the X-ray generator 12 (in other words, X-rays may be made perpendicularly incident on a detection plane of the detector 16). Although not shown, a top plate of a bed, on which the object is placed, is moved in association with the positions/directions of the X-ray generator 12 and X-ray detector 16. The positional relationship among the three is controlled such that the center of the X-ray flux may pass through the center of a region-of-interest (ROI) of the object and an imaging magnification ratio may become constant. The image magnification ratio becomes constant by making an SID (source image distance: a distance between a focal point of the X-ray tube and a detection plane of the detector) and an SOD (source object distance: a distance between the focal point of the X-ray tube and the object) constant. Instead of displacing/moving the top plate, the C-shaped arm 14 may be vertically moved and horizontally moved along the ceiling. Thereby, the position/direction of the C-shaped arm 14 itself may be varied to relatively change the direction of the object.

Reference numeral 18 denotes a holder having rollers (not shown) for clamping a rail (not shown) provided on a rear surface or a side surface of the C-shaped arm 14. Although not shown in FIG. 2, like the prior art shown in FIG. 1, the holder 18 is held to the support column so as to be rotatable about the major axis. The support column is fixed to the ceiling or floor so as to be rotatable about the support column axis. Although not shown, a vertical drive mechanism may be provided on the support column. In the case of a ceiling-pending type apparatus, a rail is provided on the ceiling so that the apparatus may be movable in one or two directions.

According to the first embodiment, the X-ray generator 12 is rotated to change the direction of irradiation, and the link mechanism 20 is driven accordingly so as to change the position/direction of the X-ray detector 16 such that the X-ray detector 16 may always be opposed to the X-ray generator 12. Thereby, even if the C-shaped arm 14 is not actually slid/rotated, the imaging angle can be altered. It is thus possible to obtain an image equivalent to an image obtained when the C-shaped arm 14 is slid/rotated at the ROI. For example, when an image is to be obtained at an oblique angle, as indicated by a broken line in FIG. 2, it is necessary in the prior art to slide/rotate the C-shaped arm 14. In the present embodiment, however, imaging can be effected by altering the direction of the X-ray generator 12 and the position of the bed and the position/direction of the X-ray detector 16 accordingly, without the need to slide/rotate the C-shaped arm 14.

As a result, the slide stroke can substantially be increased while the accessibility to the object can be maintained, without extending the C-shaped arm. If the rotation of the X-ray generator is combined with the sliding/rotating of the C-shaped arm, imaging can be effected at greater angles. If the slide stroke of the C-shaped arm is set at 180°, a 3D image can be obtained by 3D reconstruction only by sliding/rotating the C-shaped arm and rotating the X-ray generator 12 by a degree corresponding to the angle of a cone beam radiated from the X-ray generator 12.

FIG. 3 shows an example of the rotary mechanism for the X-ray generator 12. The course of rotation of the X-ray generator 12 is defined by R-shaped slide guides 22 fixed to the C-shaped arm 14. Both ends of an open-ended timing belt 24 are fixed to side surfaces of the X-ray generator 12. Pulleys 26 are engaged on both sides of an intermediate portion of the belt 24. A driving pulley 28, which is driven by a motor 30, is engaged between the belt 24 and X-ray generator 12 at a location between the pulleys 26. The timing belt 24 is driven by the rotation of the driving pulley 28. As the timing belt 24 is driven, the X-ray generator 12 rotates along the slide guides 22 and the direction of X-ray irradiation is altered.

FIGS. 4A and 4B are cross-sectional views taken along lines 4A–4A' and 4B–4B' in FIG. 3, respectively. Reference numeral 32 denotes a slide block for attaching the slide guides 22 to the C-shaped arm 14.

The angle of rotation of the X-ray generator 12 may be detected indirectly on the basis of the motor shaft by means of a potentiometer or an encoder. Alternatively, the angle of rotation of the X-ray generator 12 may be detected directly by means of a pinion engaged with a flexible rack attached to the X-ray generator 12.

Figure 5:
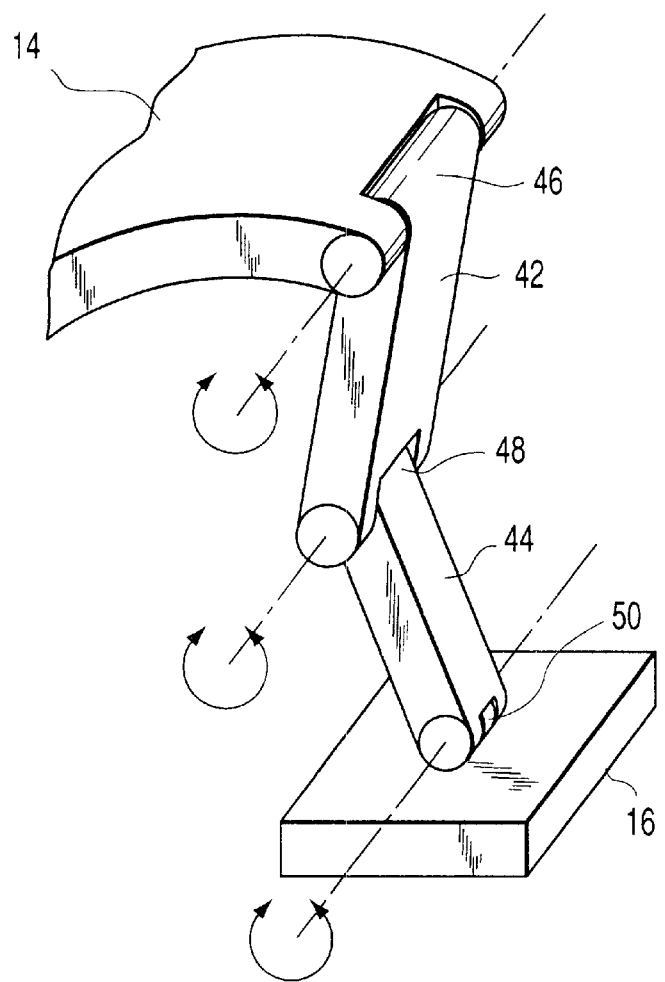
FIG. 5 is a perspective view showing a holding mechanism for an X-ray plane detector.

FIG. 5 shows an example of the link mechanism 20 for holding the X-ray detector 16 to the C-shaped arm 14 such that the position/direction of the X-ray detector 16 can be varied. The link mechanism 20 connected to the C-shaped arm 14 comprises a first arm 42, a second arm 44, a first joint 46, a second joint 48 and a third joint 50. The first joint 46 is provided at a coupling portion between the C-shaped arm 14 and first arm 42. The second joint 48 is provided at a coupling portion between the first and second arms 42 and 44. The third joint 50 is provided at a coupling portion between the second arm 44 and the X-ray detector 16. The first to third joints 46, 48, 50 have rotary functions. The first to third joints 46, 48, 50 rotate singly or in combination to achieve a desired movement. For example, the X-ray detector 16 controlled to face the X-ray generator 12 while a distance between the focal point of the X-ray generator 12 and the detection plane of the X-ray detector 16 (i.e. a surface image distance (SID)) and a distance between the focal point of the X-ray generator 12 and the object (i.e. a surface object distance (SOD)) are kept constant.

Figure 6:
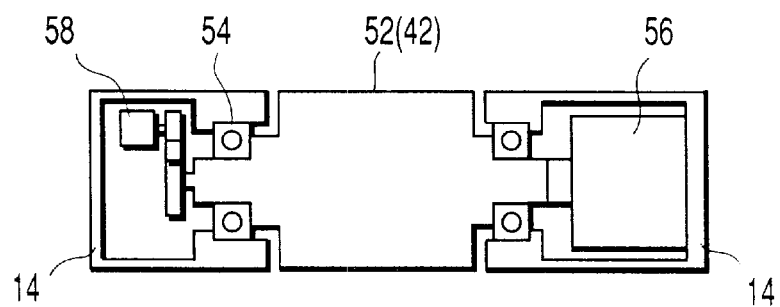
FIG. 6 is a cross-sectional view of the holding mechanism for the X-ray plane detector.

The first to third joints 46, 48 and 50 have the same structure. FIG. 6 shows the first joint 46 in detail by way of example. An end portion of the first arm 42 is integrally coupled to a drum 52. The drum 52 is rotatably attached to the C-shaped arm 14 by means of bearings 54. An end of a shaft of the drum 52 is coupled to a motor 56. The first arm 42 can be rotated by the motor 56. The other end of the shaft of the drum 52 is provided with a potentiometer or an encoder functioning as a position sensor 58 for detecting the angle of rotation of the first arm 42.

Since the link mechanism 20 has such motor-driven joints, the position/direction of the X-ray detector 16 is controlled such that the X-ray detector 16 may always face the X-ray generator 12 in accordance with the rotation of the X-ray generator 12.

Figure 7:
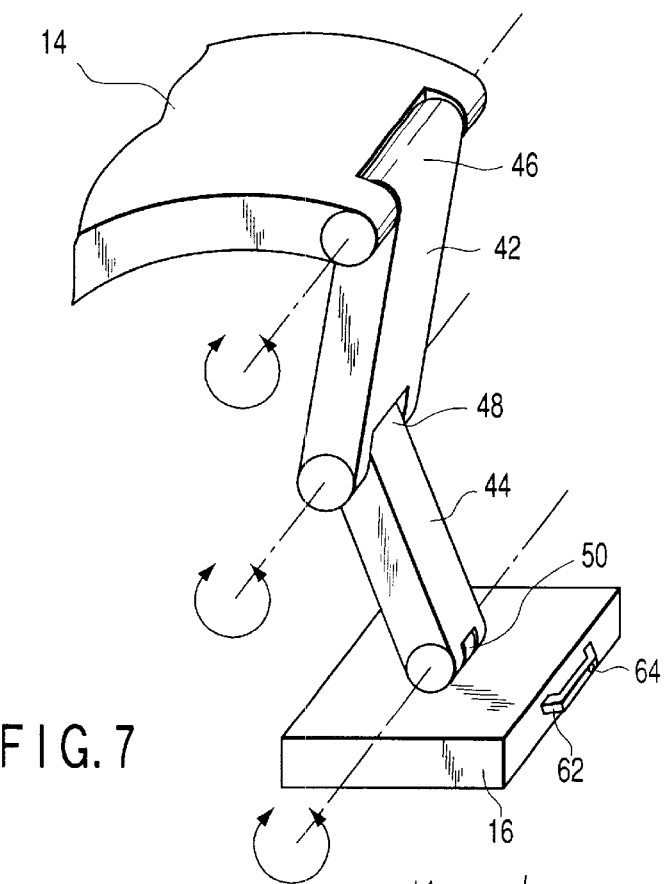
FIG. 7 shows a handle for manually moving the X-ray plane detector.

The joints may be driven by the motors or manually. In the latter case, the position/direction of the X-ray detector 16 is first determined, and then the sliding/rotation of the C-shaped arm 14 and the direction of the X-ray generator 12 are automatically altered. As is shown in FIG. 7, a handle 62 is provided on the X-ray detector 16, and the operator sets the detector 16 at a desired position/direction. If a power assist mechanism is provided and a motor is driven so as to move the X-ray detector 16 in a direction in which force is applied to the handle 62, the load for operation may reduce.

The handle 62 may be attached not to the detector 16 but to the link mechanism 20. The motor 30 (FIG. 4A) of the rotary mechanism for the X-ray generator 12 may be controlled so that the X-ray generator 12 may face the X-ray detector 16 in accordance with movement of the X-ray detector 16. Specifically, on the basis of the output of the position sensor 58 included in the link mechanism 20 of X-ray detector 16, the rotation of the X-ray generator 12 and the angle of sliding/rotating of the C-shaped arm 14 are automatically controlled in real time so that the X-ray generator 12 may face the detection plane of the X-ray detector 16.

Figure 8:
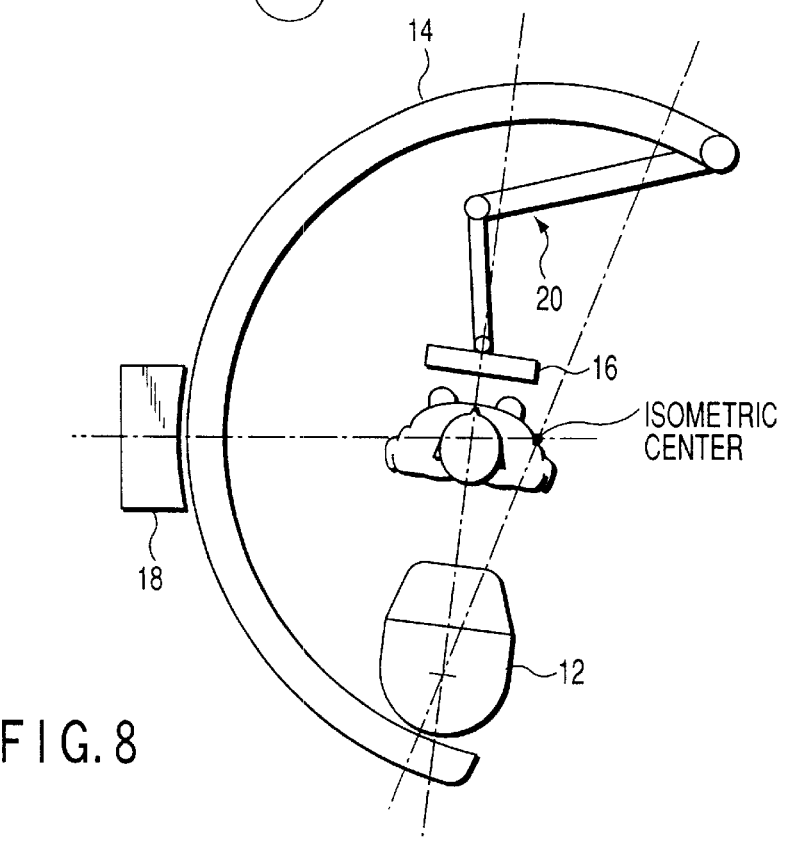
FIG. 8 shows another example of the imaging position in the first embodiment.

Thereby, the apparatus can be exactly and quickly set in the position desired by the operator. For example, as shown in FIG. 8, the apparatus can be positioned such that the isometric center departs from the ROI. Without moving the object, desired images can be obtained at various angles. Therefore, this apparatus is suitable for diagnosis in an emergency.

A brake release switch 64 is provided on the handle 62 mounted on the X-ray detector 16. When the X-ray detector 16 is manually moved, the operator holds this handle 62 and turns on the brake release switch 64. If the brake release switch 64 is turned on, braking on the three joints (coupling between the drum 52 and motor 56) of the link mechanism 20 of X-ray detector 16 and the major-axis rotation and support-column-axis rotation of the C-shaped arm is released, thus enabling manual positioning.

Force detection devices comprising, e.g. strain gauges are provided on the rotational axis of each joint and the major axis and support column axis of the C-shaped arm. The force detection devices determine imbalance due to gravity and imbalance due to external force. If the operational force is manually applied by the operator to the X-ray detector 16, rotation according to the operational force can be performed while coupling with the motor 56 is maintained. Thus, the X-ray detector 16 can be displaced/moved to the position desired by the operator.

The operator manually displaces/moves the X-ray detector 16 to the desired position/direction and turns off the brake release switch 64. Thereby, braking on the respective joints and the major-axis rotation and support-column-axis rotation of the C-shaped arm is applied, and the X-ray detector 16 is fixed at the present position.

As has been described above, according to the first embodiment, the X-ray generator 12 is rotatably fixed to the C-shaped arm 14. The X-ray detector 16 is attached to the C-shaped arm 14 such that the position/direction of the X-ray detector 16 can be altered. The X-ray generator 12 and X-ray detector 16 are rotated/moved such that they face each other. If necessary, the object is displaced/moved. Thus, without sliding/rotating the C-shaped arm 14, an image equivalent to an image obtained at angles by sliding/rotating the C-shaped arm 14 can be obtained. Accordingly, the slide stroke of the C-shaped arm can be substantially increased and images can be obtained at large angles. Since the C-shaped arm is not slid or rotated, exact and flexible positioning can be easily performed. The X-ray diagnosis apparatus applicable to a wide range of uses is provided.

Other embodiment of the apparatus of the present invention will be described below. In the following descriptions, elements common to those in the first embodiment are denoted by like reference numerals and a detailed description thereof is omitted.

Second Embodiment

The second embodiment of the invention is the same as the first embodiment in structure, but it differs in imaging mode. In the first embodiment, the SID and SOD are set at a constant value such that the imaging magnification ratio may be constant, and the normal fluoroscopic imaging mode in which x-rays are vertically incident on the detection plane of the detector 16 is adopted. In the second embodiment, the tomographic imaging mode is adopted. The second embodiment differs from the first embodiment with respect to the movement of the X-ray generator 12 and X-ray detector 16. FIG. 9 illustrates the operation at the time of imaging in the second embodiment. The joints of the link mechanism 20 are controlled and the X-ray detector 16 is moved in a plane which is in parallel to the object and the floor (thus the imaging magnification factor varies). At this time, the movement of the X-ray detector 16 and the X-ray aperture opening are controlled so that the center of the X-ray flux may coincide with the center of the detection plane of the X-ray detector 16 (but the incident angle varies). In accordance with this, the bed on which the object is placed is moved so that the region-of-interest (ROI) may always be present at the center of the X-ray flux. Like the first embodiment, instead of moving the object, the vertical movement and the movement along the ceiling (horizontal movement) of the C-shaped arm 14 may be utilized. Thereby, the C-shaped arm 14 itself may be moved to relatively move the object.

A tomographic image of the object can thus be obtained. In order to perform tomography, a tomography switch is provided as an imaging mode switch. When this switch is turned on, the tomographic mode is effected.

A modification of the second embodiment, wherein the direction of the object relative to the C-shaped arm 14 is changed 90°, will now be described. In the preceding description, the C-shaped arm 14 is disposed in a plane perpendicular to the body axis of the object. However, as shown in FIG. 10, the C-shaped arm 14 may be disposed in a plane including the body axis of the object. Thereby, inguinal region fluoroscopy, etc. can be made easily. Specifically, only the parallel movement of the X-ray detector 16 and the rotation of the X-ray generator 12 are synchronized, and the top plate on which the object is placed may not be moved. In general, in the conventional cardiac-specific apparatus, the object is accessed by the C-shaped arm from the head portion. However, in the case of the conventional offsetless C-shaped arm, the C-shaped arm interferes with the head of the object and fluoroscopy cannot be effected up to the inguinal region which is a catheter piercing region. Under the circumstances, in the prior art, in order to perform inguinal region fluoroscopy, it is necessary to use a C-shaped arm with offset (wherein the holder 18, which is a rotational axis of the arm 14, is not present in the plane defined by the arm 14). However, since the C-shaped arm with offset is inferior in balance, the power system increases in size and the accessibility to the object is not good. According to the present embodiment, however, the X-ray detector 16 can be horizontally moved in parallel from the head to the toe of the object, as shown in FIG. 10. Thereby, without moving the object, the entire body can be examined while the C-shaped arm 14 is kept static.

In the second embodiment, the x-ray detector 16 is opposed to the floor and moved horizontally. It is not necessary, however, that the detector 16 is parallel to the floor (i.e. horizontal). The detector 16 may be displaced/moved at a predetermined angle to the horizontal direction. In this case, the link mechanism is moved on the basis of the preset data representing this angle, the sliding rotational angle of the C-shaped arm 14 relative to the holder 18, the major-axis rotational angle of holder 18 relative to the support column, and the support-column-axis rotational angle of the support column to the ceiling or floor.

It is generally required in cardiac examination that imaging at large angles be performed such that blood vessels extending in various directions may not overlap. In this case, there is no choice but to dispose the detection plane of the X-ray detector 16 at an obtuse angle to the object, and the X-ray detection plane cannot be put in close contact with the object. In the case of imaging at large angles, in order to cope with this problem, an angle, at which the X-ray detector 16 is put in close contact with the object, that is, an angle, at which the tangential direction of the body surface of the object is substantially parallel to the detection plane of the X-ray detector, is precalculated and the corresponding data is stored in the apparatus as preset data. Based on the preset data, the X-ray detector 16 is positioned. The driver for the link mechanism is automatically controlled in real time to position the X-ray detector 16 at the angle of preset data, on the basis of the sliding rotational angle of the C-shaped arm 14 relative to the holder 18, the major-axis rotational angle of holder 18 relative to the support column, and the support-column-axis rotational angle of the support column to the ceiling or floor. Accordingly, the X-ray detector 16 can always be put in close contact with the object in every imaging operation, and clear images with less blurring can be obtained. The angle of the X-ray detector 16 need not be preset, but it may be set manually (including electric and manual operations) in each operation.

Switches capable of mode selection may be provided for the above-described setting of the X-ray detector 16, and the operator may set the mode. For example, four mode switches may be provided: mode 1 (opposed to the X-ray tube); mode 2 (parallel to the floor); mode 3 (variable according to each imaging operation on the basis of preset data (in close contact with the object)); and mode 4 (manual). Furthermore, a switch may be provided for displacing/moving the bed, on which the object is placed, such that the region-of-interest (ROI) may be positioned at the center of the X-ray detection plane. When this switch is turned on, the bed is displaced/moved. When this switch is turned off, the bed is stopped. Besides, a 3D scan mode (FIG. 2) switch or a tomography mode (FIG. 9) switch may be provided.

Third Embodiment

Figure 11:
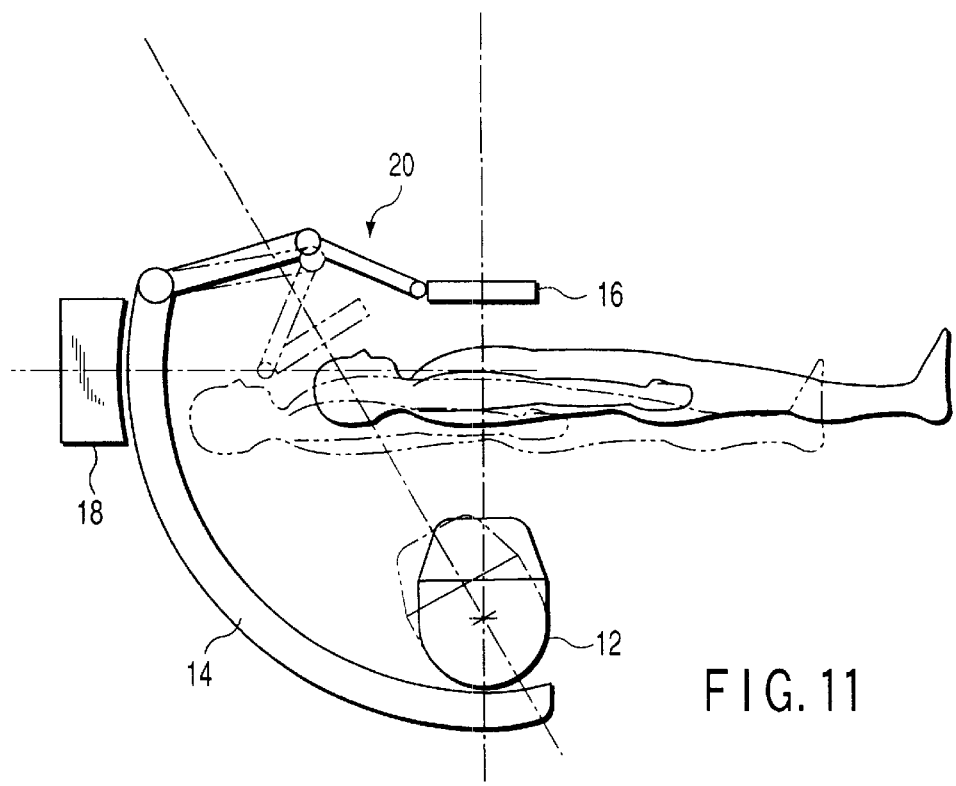
FIG. 11 shows a basic structure of a C-shaped arm of an X-ray diagnosis apparatus according to a third embodiment of the present invention.

The C-shaped arm 14 in the first and second embodiments has a substantially semicircular shape as in the prior art. In the present invention, since the sliding/rotational angle is substantially increased by the rotation of the X-ray tube, the length of the C-shaped arm 14 can be shortened. FIG. 11 shows the structure of the C-shaped arm according to the third embodiment. The basic structure is common to the first and second embodiments, but the C-shaped arm 14 is shortened and has an arcuated shape substantially corresponding to a quarter of a circle.

Like the first and second embodiments, the X-ray generator 12 is rotated and the position/direction of the X-ray detector 16 and the position of the bed are varied accordingly. It is thus possible to obtain a slide stroke equivalent to the slide stroke of the substantially semicircular C-shaped arm of the conventional circulatory-system X-ray diagnosis apparatus. As a result, the entire apparatus can be reduced in size and weight, and the installation space in the hospital can be saved. In the third embodiment, like the first and second embodiments, imaging can be performed in various modes.

Fourth Embodiment

Figure 12:
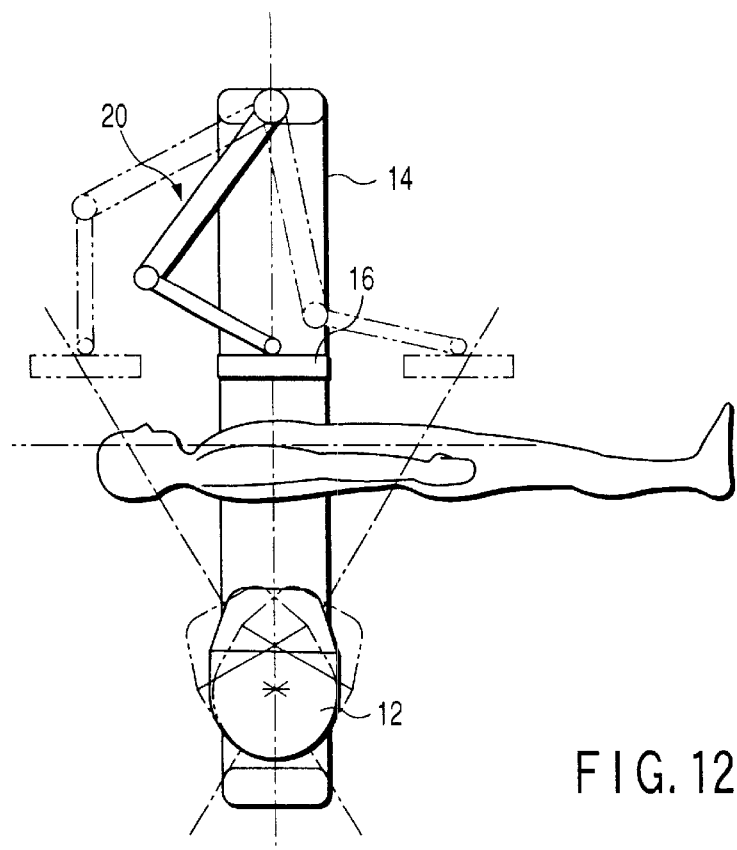
FIG. 12 shows a basic structure of a C-shaped arm of an X-ray diagnosis apparatus according to a fourth embodiment of the present invention.

In the preceding three embodiments, the axial direction of the joints of the link mechanism 20 of X-ray detector 16 is perpendicular to a plane defined by the C-shaped arm 14. However, the axial direction of the joints may be set in the plane defined by the C-shaped arm 14. FIG. 12 shows the C-shaped arm according to the fourth embodiment of the invention, wherein the first embodiment is modified in this manner. In the fourth embodiment, like the first and second embodiments, imaging can be performed in various modes. Although not shown, the second and third embodiments may be modified similarly.

Fifth Embodiment

Figure 13:
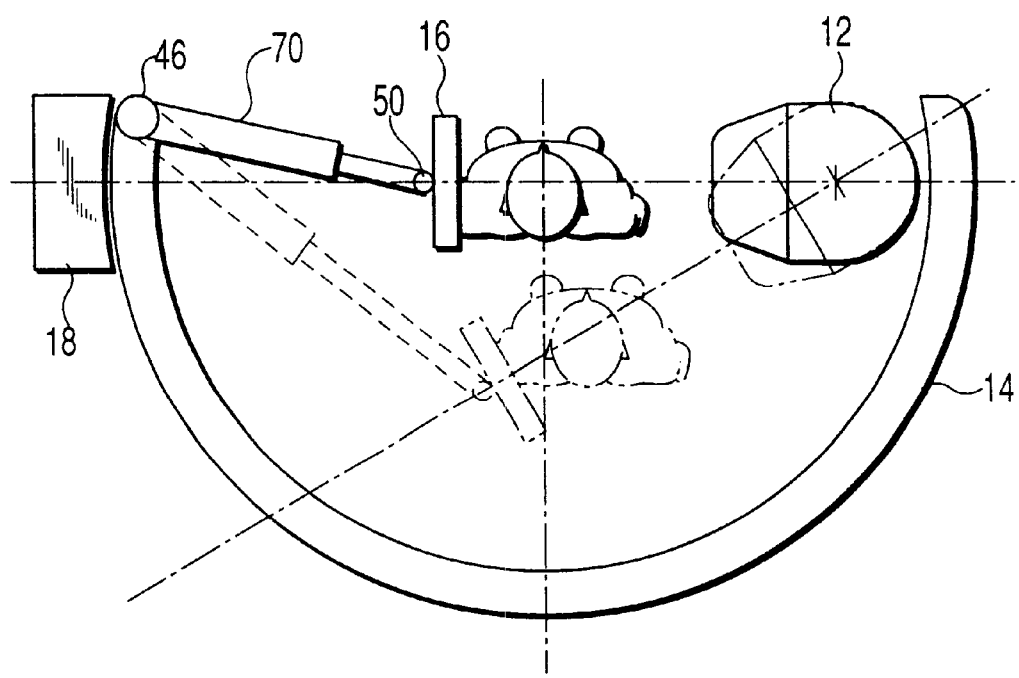
FIG. 13 shows a basic structure of a C-shaped arm of an X-ray diagnosis apparatus according to a fifth embodiment of the present invention.

FIG. 13 shows a C-shaped arm of an X-ray diagnosis apparatus according to the fifth embodiment of the invention. The fifth embodiment relates to a modification of the link mechanism of the first embodiment. In the first embodiment, the link mechanism for holding the X-ray detector 16 is constructed such that the position/direction of the X-ray detector 16 can be varied by the first and second arms 42 and 44 coupled by means of the joint 48. However, the same advantage as with the first embodiment can be obtained, even if a proximal end of an extendible arm 70 is coupled to the C-shaped arm 14 by means of the first joint 46 of the first embodiment and a distal end of the arm 70 is coupled to the X-ray detector 16 by means of the third joint 50 of the first embodiment. Although not shown, the second to fourth embodiments can be modified similarly.

Figure 14:
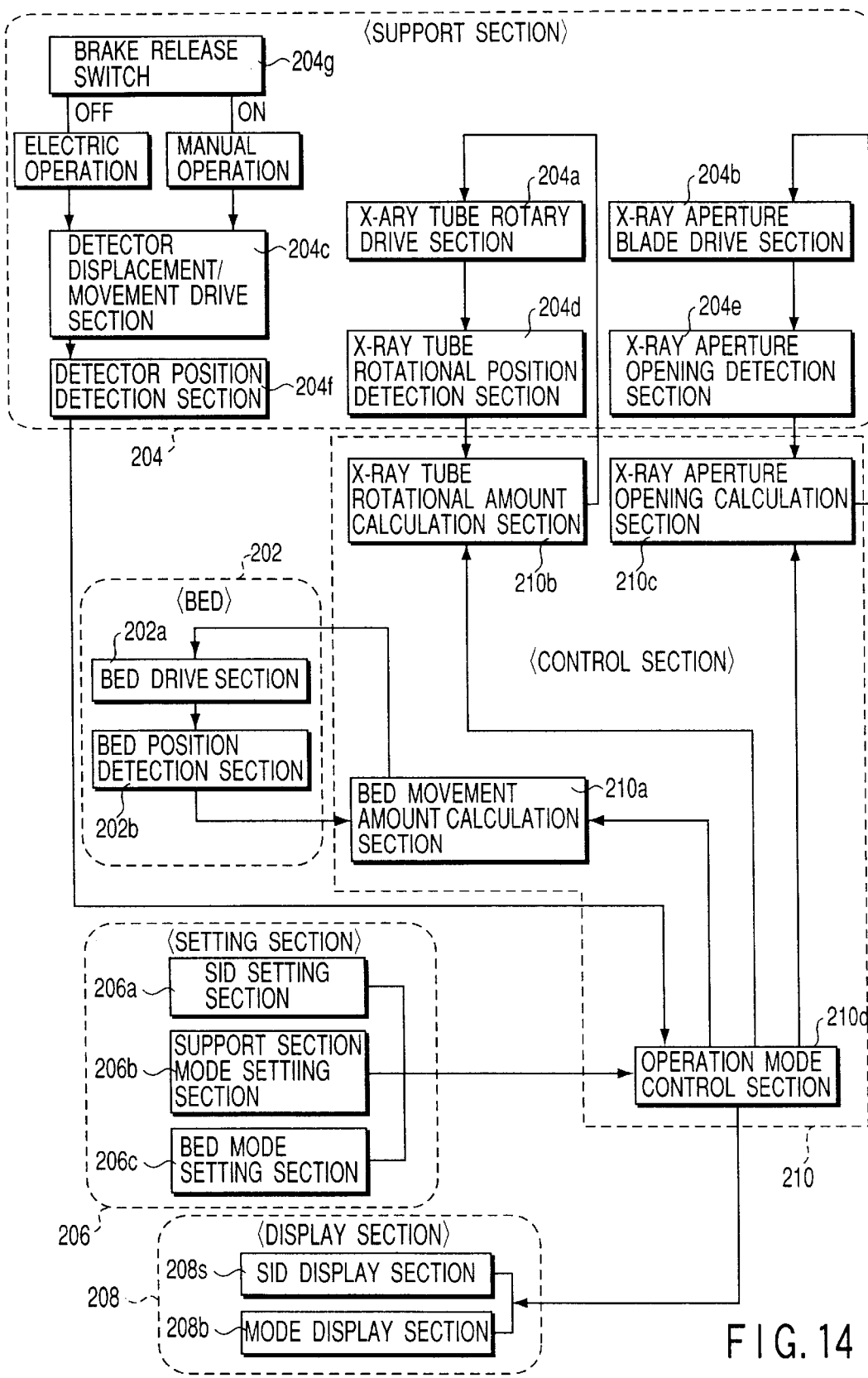
FIG. 14 is a block diagram showing the configuration of a control circuit of the X-ray diagnosis apparatus according to the present invention.

FIG. 14 is a block diagram showing a circuit configuration of the X-ray diagnosis apparatus according to the present invention. This circuit configuration is applicable to the first to fifth embodiments.

The X-ray diagnosis apparatus of this invention generally comprises a bed 202, a support section 204, a setting section 206, a display section 208 and a control section 210. The bed 202 comprises a bed drive section 202a for moving a top plate in the vertical direction, left-and-right direction, and front-and-rear direction, and a bed position detection section 202b for detecting a movement position. An output from the bed position detection section 202b is fed to a bed movement amount calculation section 210a in the control section 210. Based on a calculation result in the bed movement amount calculation section 210a, the bed drive section 202a feed-back controls the bed position.

The support section 204 corresponds to the mechanism for rotatably attaching the X-ray generator 12 to the C-shaped arm 14, and to the link mechanism 20 for movably attaching the X-ray detector 16 to the C-shaped arm 14. The support section 204 comprises an X-ray tube rotary drive section 204a corresponding to the motor 30 in FIG. 3, an X-ray aperture blade drive section 204b, and a detector displacement/movement drive section 204c corresponding to the motor 56 in FIG. 6. An output from the X-ray tube rotary drive section 204a is fed to an X-ray tube rotational position detection section 204d such as a potentiometer or an encoder. An out put from the X-ray tube rotational position detection section 204d is delivered to an X-ray tube rotational amount calculation section 210b in the control section 210. Based on a calculation result of the X-ray tube rotational amount calculation section 210b, the X-ray tube rotary drive section 204a feed-back controls the rotational position of the X-ray tube. An output from the X-ray aperture blade drive section 204b is fed to an X-ray aperture opening detection section 204e. An output from the X-ray aperture opening detection section 204e is fed to an X-ray aperture opening calculation section 210c in the control section 210. Based on a calculation result in the X-ray aperture opening calculation section 210c, the X-ray aperture blade drive section 204b feed-back controls the aperture opening for X-rays.

The support section 204 further includes a brake release switch 204g. An ON/OFF signal is fed by a manual operation or an electric operation to the detector displacement/movement drive section 204c. An output from the detector displacement/movement drive section 204c is delivered to an operation mode control section 210d in the control section 210 via a detector position detection section 204f corresponding to the position sensor 58 in FIG. 6.

The operation mode control section 210d controls the bed displacement/movement amount calculation section 210a, X-ray tube rotational amount calculation section 210b and X-ray aperture opening calculation section 210c. A setting signal from the setting section 206 comprising an SID setting section 206a, a support section mode setting section 206b and a bed mode setting section 206c is also delivered to the operation mode control section 210d. An output from the operation mode control section 210d is fed to the display section 208 comprising an SID display section 208a and a mode display section 208b.

This control circuit realizes the various operations as described above.

As has been described, according to the present invention, the X-ray generator for emitting X-rays to the object is attached to the C-shaped arm such that the position/direction of the X-ray generator can be varied. By varying the position/direction of the X-ray generator, the direction of emission of X-rays can be changed. The planar X-ray detector comprising the solid-state detector array, which is less than the conventional I.I. in size and weight, is used to detect X-rays which have passed through the object. The X-ray detector is attached to the C-shaped arm by means of the mechanism which can easily alter the position/direction of the X-ray detector in accordance with the direction of emission of X-rays determined by the position/direction of the X-ray generator. The bed on which the object is placed is moved to the position corresponding to the position/direction of the X-ray generator. Unlike the conventional C-shaped arm, the C-shaped arm of this invention can be positioned at large angles. The degree of freedom of the apparatus increases and this apparatus is applicable to a wide range of clinical uses. Moreover, the slide stroke can be substantially increased without deteriorating the accessibility to the object, and volume image acquisition is realized. Tomographic images can also be obtained with ease, and the degree of freedom of the apparatus increases. Furthermore, the apparatus can be reduced in size and weight. For example, volume data acquisition by sliding rotation is realized, and tomographic images can be easily obtained.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents. For example, the link mechanism 20 for holding the X-ray detector comprises two arms and three joints. However, the number of arms can be increased to five and the number of joints to six, and three-dimensional displacement/movement can be achieved by alternately changing the directions of axes of the joints. If the columnar joints are replaced with spherical joints, three-dimensional movement is realized with use of the two arms. The present invention is applicable not only to the circulatory-system X-ray diagnosis apparatus, but also to X-ray diagnosis apparatuses for other regions or diagnosis apparatuses having X-ray generators.

What is claimed is:

1. An X-ray diagnosis apparatus comprising:
    an X-ray generator configured to emit X-rays towards an object;
    an X-ray detector configured to detect the X-rays which have passed through the object;
    a first arm having an arcuated shape;
    an arm support member configured to support the first arm;
    an X-ray generator support member, provided at one end of the first arm, configured to support the X-ray generator such that a position and/or a direction of the X-ray generator is variable in order to direct X-rays toward an outside region of the first arm; and
    a detector support member, provided at another end of the first arm, configured to support the X-ray detector such that a position and/or a direction of the X-ray detector is variable in order to receive X-rays.

2. The apparatus according to claim 1, wherein the arm support member comprises a holder configured to support the first arm such that the first arm is slidable along the arm support member, and a support column configured to rotatably support the holder.

3. The apparatus according to claim 2, wherein the first arm is such an offsetless arm that a rotational axis of the holder is located in a plane defined by the arm.

4. The apparatus according to claim 1, wherein the detector support member comprises a plurality of arms and a joint configured to movably couple the arms, one of the arms being movably coupled to said the another end of the first arm, and another of the arms being movably coupled to the detector.

5. The apparatus according to claim 1, wherein the X-ray generator support member comprises a plurality of arms and a joint configured to movably couple the arms, one of the arms being movably coupled to said one end of the first arm, and another of the arms being movably coupled to the X-ray generator.

6. The apparatus according to claim 1, wherein the detector support member comprises a single extendible arm movably coupled at one end to said another end of the first arm and movably coupled at the other end to the detector.

7. The apparatus according to claim 1, wherein the X-ray generator support member comprises a single extendible arm movably coupled at one end to said one end of the first arm and movably coupled at the other end to the X-ray generator.

8. The apparatus according to claim 1, wherein the detector support member controls the position and/or the direction of the detector such that a center of emitted X-rays coincides with a center of an image reception plane of the detector, and
    the X-ray generator controls an X-ray aperture opening in accordance with a positional relationship between the X-ray generator and the X-ray detector.

9. The apparatus according to claim 1, wherein the detector support member controls the position and/or the direction of the X-ray detector such that the X-ray detector faces the X-ray generator.

10. The apparatus according to claim 9, wherein the detector support member supports the X-ray detector such that a distance between a focus point of the X-ray generator and a detection plane of the X-ray generator is kept constant.

11. The apparatus according to claim 1, wherein the detector support member controls the position and/or the direction of the X-ray detector such that the X-ray detector is parallel to a floor.

12. The apparatus according to claim 11, which further comprises:
    a bed apparatus configured to parallel-move the object in a plane parallel to the floor, and
    wherein the X-ray generator support member changes the position and/or the direction of the X-ray generator in association with movement of the object, and
    the detector support member parallel-moves the X-ray detector in a plane parallel to the floor in association with the movement of the object.

13. The apparatus according to claim 11, wherein the X-ray generator support member changes the position and/or the direction of the X-ray generator such that a direction of the X-rays varies along a body axis of the object, and
    the detector support member parallel-moves the X-ray detector in a plane parallel to the floor in association with a change in the position/direction of the X-ray generator.

14. The apparatus according to claim 1, wherein the detector support member controls the direction of the X-ray detector at a predetermined angle to the floor.

15. The apparatus according to claim 1, wherein the detector support member controls the position/direction of the X-ray detector such that the X-ray detector is substantially put in close contact with a body surface of the object.

16. The apparatus according to claim 1, which further comprises a handle provided on a part of one of the detector support member and the detector, and
    wherein the X-ray generator support member moves the X-ray generator in association with movement of the X-ray detector when the X-ray detector is manually moved with use of the handle.

17. The apparatus according to claim 1, wherein the detector support member comprises an input unit configured to set a distance between a focal point of the X-ray generator and a detection plane of the X-ray detector, a controller configured to control the position and/or the direction of the X-ray detector such that said distance is kept constant, and a display configured to display said set distance.

18. The apparatus according to claim 1, further comprising a controller configured to control a position of a bed, on which the object is placed, such that a center of an X-ray flux passes through a center of a region-of-interest of the object while an imaging magnification ratio is kept constant.

19. The apparatus according to claim 1, wherein the detector support member includes a driver configured to move the X-ray detector in a given plane, and the X-ray generator support member includes a controller configured to control an X-ray aperture opening of the X-ray generator such that a center of an X-ray flux coincides with a center of a detector image-reception plane of the X-ray detector.

20. The apparatus according to claim 19, further comprising a controller configured to control a position of a bed, on which the object is placed, such that a region-of-interest is always located at a center of an image.

21. The apparatus according to claim 1, wherein the detector support member comprises a brake release switch configured to manually turn on and off braking of respective movable mechanisms.

22. The apparatus according to claim 21, further comprising a controller configured to control respective movable portions holding the detector support member such that manual operations can be performed when the position and/or the direction of the X-ray detector is controlled.

23. The apparatus according to claim 20, wherein the X-ray generator support member includes a controller configured to control an X-ray aperture opening of the X-ray generator such that a center of an X-ray flux coincides with a center of an image-reception plane of the X-ray detector.

24. The apparatus according to claim 1, wherein the first arm has an arcuated shape of about 90°.

25. The apparatus according to claim 1, wherein the X-ray detector is a planar detector comprising a plurality of solid-state detection elements.

26. The apparatus according to claim 1, wherein the object is arranged such that a body axis is included in an arm plane defined by the first arm, said X-ray generator support member supports the X-ray generator such that the X-ray generator is shifted within the arm plane, and said detector support member supports the detector such that the detector is shifted within the arm plane, and which further comprises a support member controller configured to vary the positions and/or the directions of the X-ray generator and the detector such that the direction of the X-ray changes along the body axis.

27. The apparatus according to claim 1, wherein the object is arranged such that a body axis is perpendicular to an arm plane defined by the first arm, said X-ray generator support member supports the X-ray generator such that the X-ray generator is shifted within the arm plane, and said detector support member supports the detector such that the detector is shifted within the arm plan, and which further comprises a support member controller configured to vary the positions and/or the directions of the X-ray generator and the detector such that the direction of the X-ray changes perpendicular to the body axis.

28. The apparatus according to claim 1, wherein the object is arranged such that a body axis is included in an arm plane defined by the first arm, said X-ray generator support member supports the X-ray generator such that the X-ray generator is shifted within a plane perpendicular to the arm plane, and said detector support member supports the detector such that the detector is shifted within the plane perpendicular to the arm plane, and which further comprises a support member controller configured to vary the positions and/or the directions of the X-ray generator and the detector such that the direction of the X-ray changes along the body axis.

* * * * *